(12) United States Patent
Lebrun et al.

(10) Patent No.: US 6,689,749 B1
(45) Date of Patent: Feb. 10, 2004

(54) NEUROPEPTIDES ORIGINATING IN SCORPION

(75) Inventors: Bruno Lebrun, Marseilles (FR); Régine Romi-Lebrun, Marseilles (FR); Hiroyuki Minakata, Kawabe-gun (JP); Terumi Nakajima, Tokyo (JP); Junko Hashino, Kyoto (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/125,811

(22) PCT Filed: Dec. 25, 1997

(86) PCT No.: PCT/JP97/04810
§ 371 (c)(1),
(2), (4) Date: Aug. 26, 1998

(87) PCT Pub. No.: WO98/29446
PCT Pub. Date: Jul. 9, 1998

(30) Foreign Application Priority Data

Dec. 19, 1996 (JP) .............................. 8-359815
Oct. 30, 1997 (JP) .............................. 9-312871

(51) Int. Cl.⁷ .................. A61K 38/16; C07K 14/00
(52) U.S. Cl. ................. 514/9; 514/10; 514/12; 530/317; 530/324; 424/236.1; 435/71.3
(58) Field of Search ................. 530/324, 317; 514/12, 9, 10; 435/71.3; 424/236.1

(56) References Cited

PUBLICATIONS

Ngo et al., 'Computational Complexity, Potein Structure Prediction, and the Levinthal Paradox,' The Protein Folding Problem and Tertiary Structuer Prediction. Ed. K. Merz and L. Le Grand. BirkHauser, Boston MA. pp. 491–495, 1994.*

Rogowski, Robert S. et al., "Three new toxins from the scorpion Pandinus imperator selectively block certain voltage–gated K⁺ channels.", Mol. Pharmacol., 50(5) (1996), p. 1167–1177.

Gomez–Lagunas, "Two novel toxins from the venom of the scorpion Pandinus imperator show that the N–terminal amino acid sequence is important for their affinities towards Shaker B K⁺ channels.", J. Membr. Biol., 152 (1) (1996), p. 49–56.

Sabatier, J.–M, "Synthesis and characterization of Leiurotoxin I analogs lacking one disulfide bridge: evidence that disulfide pairing 3–21 is not required for full toxin activity.", Biochemistry, 35 (33) (1996), p. 10641–10647.

Kharrat, R., "Maurotoxin, a four disulfide bridge toxin from Scorpion maurus venom: purification, structure and action on potassium channels.", FEBS Lett., 406(3) (1997), p. 284–290.

M. Delepierre, "A Novel Potassium Channel Blocking Toxin from the Scorpion Pandinus imperator: A 1H NMR Analysis Using a Nano–NMR probe.", Biochemistry, 36 (9) (1997), p. 2649–2658.

Kharrat, Ryadh, "Chemical synthesis and characterization of maurotoxin, a short scorpion toxin with four disulfide bridges that acts on K⁺ channels.", Eur. J. Biochem., 242 (3) (1996), p. 491–498.

Neito, Alejandro, "Noxiustoxin 2, a novel K⁺ channel blocking peptide from the venom of the scorpion Centruroides noxius Hoffmann.", Toxicon, 34 (8) (1996), p. 913–922.

Blanc, E. "Solution structure of P01, a natural scorpion peptide structurally analogous to scorpion toxins specific for apamin–sensitive potassium channel.", Proteins, 24 (3) (1996), p. 359–369.

* cited by examiner

Primary Examiner—Christopher S. F. Low
Assistant Examiner—Anish Gupta
(74) Attorney, Agent, or Firm—Crowell & Moring, L.L.P.

(57) ABSTRACT

The invention provides a peptide capable of blocking voltage-gated K⁺ channels and inhibiting IL-2 production, which is represented by an amino acid sequence of:

Ala-Ser-Cys-Arg-Thr-Pro-Lys-Asp-Cys-Ala-Asp-Pro-Cys-Arg-Lys-Glu-Thr-Gly-Cys-Pro-Tyr-Gly-Lys-Cys-Met-Asn-Arg-Lys-Cys-Lys-Cys-Asn-Arg-Cys;

in which the C-terminal is amidated and four disulfide bridges are present in the molecule, and their related peptides isolated from the venom gland of a scorpion *Heterometrus spinnifer*.

The peptides provided by the present invention are neuropeptides which can block voltage-gated K⁺ channels and inhibit IL-2 production at an extremely low concentration and, therefore, are expected to contribute to application of scorpion toxins to medicines and so on.

7 Claims, 2 Drawing Sheets

O : NATURAL HsTX1
■ : SYNTHETIC HsTX1
▲ : HsTX1−COOH

*p < 0.01
(RELATIVE TO CONTROL VALUE)

SEQUENCE LISTING

<160> NUMBER OF SEQ ID NOS: 1

<210> SEQ ID NO 1
<211> LENGTH: 34
<212> TYPE: PRT
<213> ORGANISM: Heterometrus spinnifer

<400> SEQUENCE: 1

```
Ala Ser Cys Arg Thr Pro Lys Asp Cys Ala Asp Pro Cys Arg Lys
 1               5                  10                  15

Glu Thr Gly Cys Pro Tyr Gly Lys Cys Met Asn Arg Lys Cys Lys
                20                  25                  30

Cys Asn Arg Cys
```

NEUROPEPTIDES ORIGINATING IN SCORPION

TECHNICAL FIELD

The invention relates to novel neuropeptides, more specifically scorpion toxin-related peptides which are obtained from the venom gland of *Heterometrus spinnifer*, a species of scorpion.

BACKGROUND ART

"Scorpion" is a general term for arthropods belonging to the class Arachnida, the order *Scorpionida* and about 600 species of scorpions now inhabit the world. Scorpions have generally believed to be virulently poisonous; however, actually those having fetal toxins are limited to only several species, including *Buthus ustralis* (living in the deserts of Africa), *Centruroides exilicauda* (native to Mexico) and *B. occitauda* (native to South Europe), etc. Up to now, various types of scorpion toxins have been isolated (Dreyer. F., Rev. Physiol. Biochem. Pharmacol., vol.15, pp.94–128, 1990), which are considered to be neurotoxins.

From the studies on pharmacological properties of these toxins, the actions of the toxins against $K^+$ channels have been drawing attention. For example, margatoxin (MgTX) isolated from the venom gland of *Centruroides margaritatus* (Garcia-Calvo et al., J. Biol. Chem., vol. 268, pp. 18866–18874, 1993) and agitoxin 2 (AgTX2) isolated from the venom gland of *Leiurus quinquestriatus herbraes* (Garcia et al., Biochemistry, vol. 33, pp. 6834–6839, 1994) have been known to act as blockers on voltage-gated $K^+$ channels. These toxins are peptides composed of 38 amino acid residues and containing three disulfide bridges in their molecules. Recently, also reported is a peptide, *Pandinus imperator* toxin 1 (Pi1), which is a peptide containing four disulfide bridges in the molecule and composed of 35 amino acid residues (Olamendi-Portugal et al., Biochem. J. vol. 315, pp. 977–981, 1996).

On the other hand, it has been considered that production of interleukin-2 (IL-2) by T cells requires $Ca^{2+}$ influx into the T cells. Recently, it has been discovered that Kv1.3, which is one type of the $K^+$ channels, is involved in $Ca^{2+}$ influx into T cells accompanied by activation of the T cells (Leonard et al., Proc. Natl. Acad. Sci. USA, vol. 89, pp. 10094–10098, 1992). Further, Lin et al. reported that inhibition of Kv1.3 channels suppresses $Ca^{2+}$ influx into T cells, proliferation of T cells and production of IL-2 by T cells (J. Exp. Med., vol. 177, pp.637–645, 1993).

Under these circumstances, scorpion toxins are expected to be applicable to medicines in view of their various pharmacological activities. However, for application to medicines, it is necessary to separate the useful pharmacological activities of the toxins from their undesirable toxicity and, consequently, it becomes necessary to isolate much scorpion toxins and clarify the structure-activity relationship thereof. In these situations, the object of the present invention is to provide novel scorpion toxin-related peptides for contribution to application of scorpion toxins to medicines.

DISCLOSURE OF THE INVENTION

The inventors have made intensive and extensive studies on isolation of novel scorpion toxin-related peptides from the venom gland of a scorpion *Heterometrus spinnifer*, on the basis of the ability to block the rat brain voltage-gated $K^+$ channels Kv1.3 (also called "RCK3") expressed in *Xenopus oocytes*. As a result, the inventors have succeeded in isolation and purification of a novel peptide, named HsTX1, represented by SEQ ID NO:1 in which four disulfide bridges are present in the molecule. They have also succeeded in determination of the primary and higher-order structures of HsTX1. It has been found that HsTX1 exhibits much stronger ability to block the $K^+$ channels compared with the previously reported scorpion toxins and inhibits the IL-2 production by human peripheral blood T cells. Thus, the invention has been accomplished.

According to the present invention, there is provided a peptide represented by an amino acid sequence:

```
Ala Ser Cys Arg Thr Pro Lys Asp
Cys Ala Asp Pro Cys Arg Lys Glu
Thr Gly Cys Pro Tyr Gly Lys Cys
Met Asn Arg Lys Cys Lys Cys Asn
Arg Cys; (SEQ ID NO:1)
``` in which 0 to 4 disulfide bridges are present in the molecule and the C terminal may be amidated, as a blocker of voltage-gated $K^+$ channels or an inhibitor of IL-2 production.

In a specific embodiment, the present invention provides a peptide represented by the above amino acid sequence in which the disulfide bridges are selected from the group consisting of $CyS^3$-$Cys^{24}$, $Cys^9$-$Cys^{29}$, $Cys^{13}$, $Cys^{31}$ and $Cys^{19}$-$Cys^{34}$.

In a most preferred embodiment, the present invention provides a peptide represented by the above amino acid sequence in which the C terminal is amidated and four disulfide bridges, $Cys^3$-$Cys^{24}$, $CyS^9$-$Cys^{29}$, $Cys^{13}$-$Cys^{31}$ and $Cys^{19}$-$Cys^{34}$, are present in the molecule.

BEST MODE FOR CARRYING OUT THE INVENTION

Figure 1:
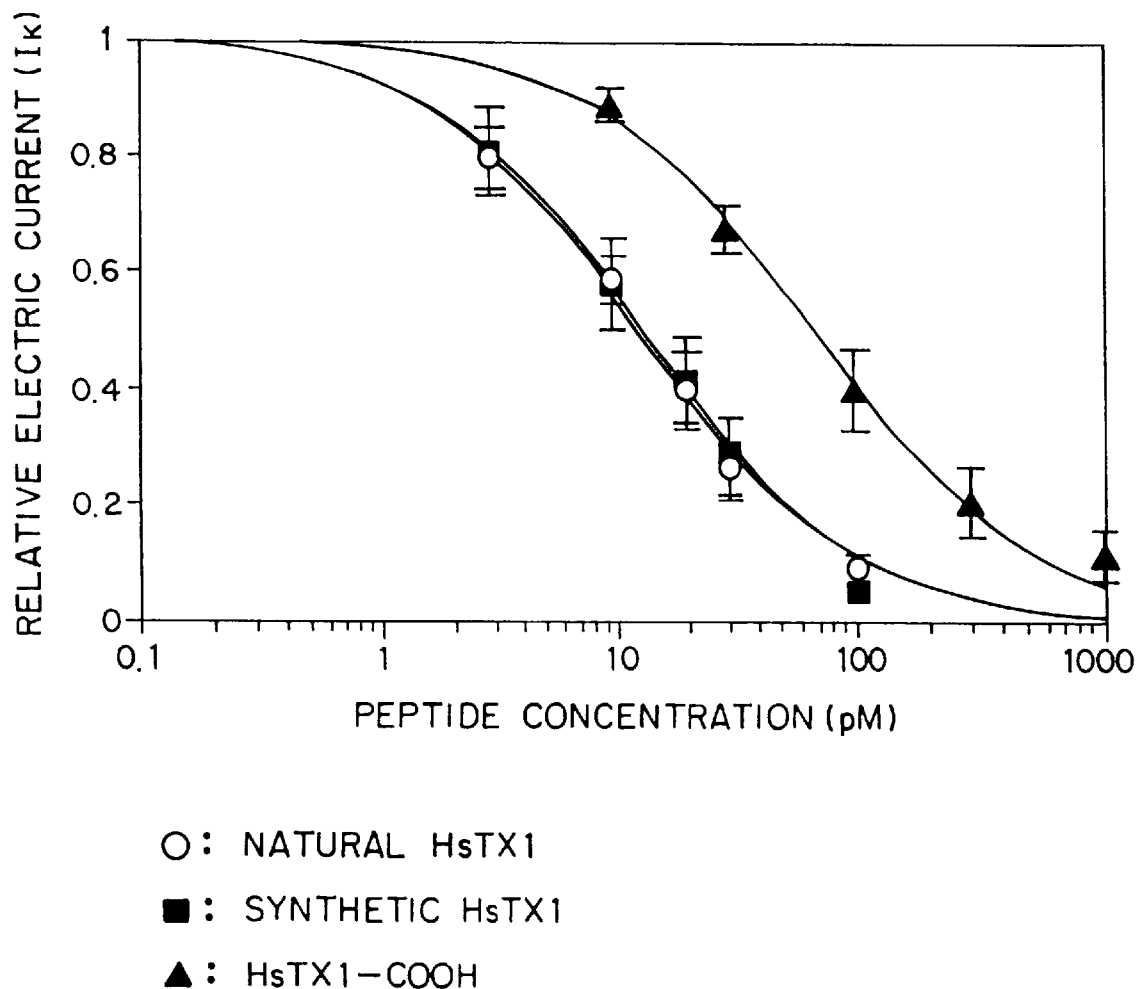
FIG.1 is a graph illustrating the blocking activity of the peptides according to the invention on the rat Kv1.3 channels, depending on the concentration of the peptides; wherein the open circle (○) indicates the data for natural HsTX1, the solid square (■) indicates the data for synthetic HsTX1, and the solid triangle (▲) indicates the data for HsTX1-COOH having the C-terminal of —COOH.
Figure 2:
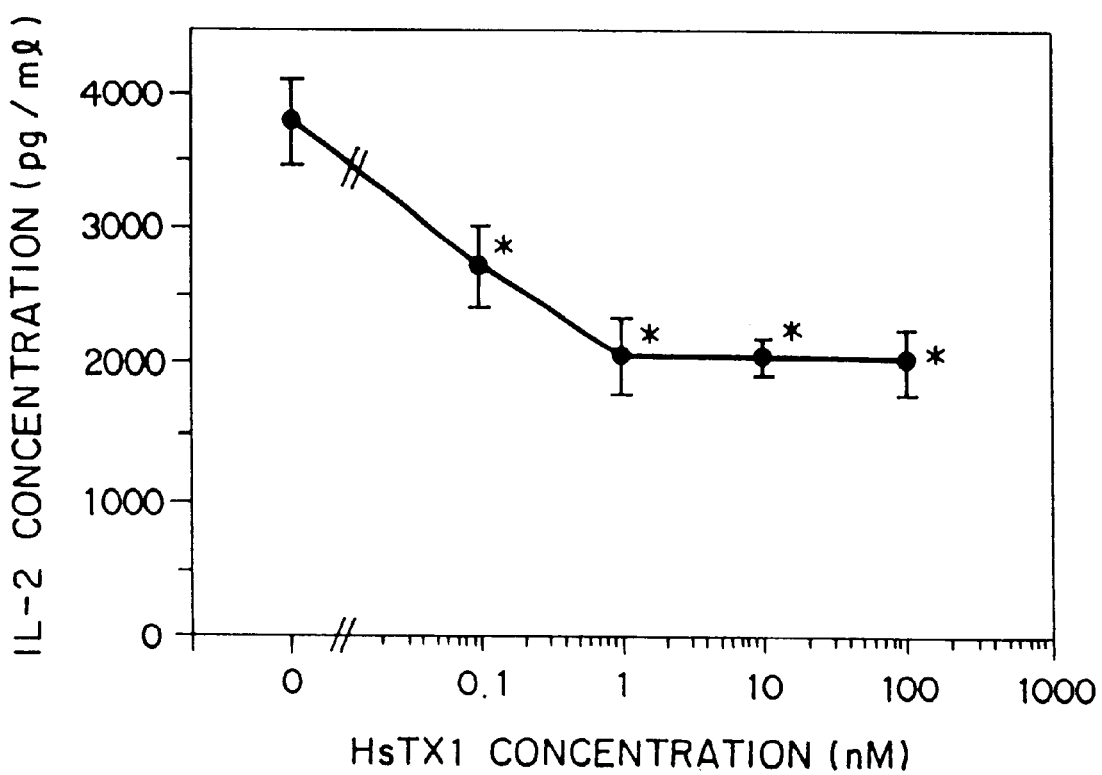
FIG. 2 is a graph illustrating the inhibitory action of HsTX1 on the IL-2 production by human peripheral blood T cells stimulated with PMA and ionomycin, depending on the concentration of HsTX1.

The peptides of the present invention can be obtained by taking out the venom gland from a scorpion containing the peptide of the present invention, such as *Heterometrus spinnifer*, subjecting it to extraction with, for example, about 0.5 M of acetic acid to give a crude extract of the peptide, then isolating and purifying the peptide from the crude extract by a conventional technique such as ion exchange chromatography and reversed-phase chromatography.

As for HsTX1, which is a naturally occurring peptide and one of the peptides of the present invention, it is apparent that the C-terminal is amidated and four disulfide bridges are present in the molecule, in view of the following:

(1) amino acid sequence analysis of the peptide revealed the presence of eight Cys residues in the molecule;

(2) mass spectrometry of the peptide revealed that the peptide occurs as a monomer; and (3) good agreement between the molecular weight of the peptide experimentally determined and the calculated molecular weight of the peptide on the assumption that the C-terminal is amidated and four disulfide bridges are present in the molecule.

In the peptides of the present invention, the number and position of disulfide bridges are not particularly limited. Among the peptides of the present invention, the naturally occurring one was found to contain four disulfide bridges at the position of $Cys^3$-$Cys^{24}$, $Cys^9$-$Cys^{29}$, $Cys^{13}$-$Cys^{31}$ and $Cys^{19}$-$Cys^{34}$, as apparent from the examples mentioned later. This natural peptide may also be obtained by randomly introducing four disulfide bridges into a peptide containing no disulfide bridge and then screening and purifying a peptide having the same structure as that of the natural one.

A peptide containing no disulfide bridge can be conveniently synthesized by a solid phase method using a conventional peptide synthesizer (e.g., 433A peptide synthesizer, available from Applied Biosystems). Disulfide bridges can be introduced into the peptide molecule by an oxidation reaction such as oxidation by air exposure or with potassium ferricyanide (Hope et al., J. Biol. Chem., vol. 237, pp. 1563–1566, 1962). Screening and purification of the peptide identical to the natural peptide from the disulfide bridge-introduced peptides can be conducted, for example, by a method using reversed-phase C-18 high performance liquid chromatography (C-18 HPLC), in which the fraction (s) indicating the same retention time as that of the natural peptide is isolated.

The peptides of the present invention may also be obtained by appropriately employing a gene recombination technique in a conventional manner.

The above-mentioned synthesis methods also enable to produce other type of peptides which have the same primary structures as that of the natural one but have the number and fashion of disulfide bridges different from those of the natural one. Therefore, such peptides are also covered within the scope of the invention, as long as they are represented by SEQ ID NO: 1 in which 0 to 4 disulfide bridges are present in such a manner that Cys residues at any positions in the molecule are linked through disulfide bridge(s).

The peptides may include deletions, additions or substitutions of a portion of the amino acid residue, so long as they have the same pharmacological activities as that of the natural peptide of the present invention. Such peptides are also covered within the technical scope of the invention as peptides useful as blockers of voltage-gated $K^+$ channels or inhibitors of IL-2 production.

As demonstrated in Evaluation Example 2 shown below, peptides having the C-terminal of —COOH also possess an inhibitory activity on the $K^+$ channels, and therefore are also covered within the technical scope of the invention.

Among them, the natural peptide is the first discovered one of neuropeptides composed of 34 amino acid residues and containing four disulfide bridges in the molecule. The natural peptide can block rat brain voltage-gated $K^+$ channels Kv1.3 expressed in *Xenopus oocytes* at an extremely low concentration and can also inhibit the IL-2 production by human peripheral blood T cells. Accordingly, the peptides provided by the present invention and analogues thereof would contribute to application of scorpion toxin-related peptides to biochemical reagents in neurophysiology as well as application to human or veterinary medicines. Examples of medicines to which the peptides and analogues thereof can be applied include immunosuppressive agents for organ transplantation, graft-versus-host diseases (GVHD) and autoimmune diseases.

When the peptides of the present invention are used as medicines, the dosage forms are not particularly limited and may be for oral or parenteral administration. The peptides can be prepared into various types of formulations, including injection solutions, infusion solutions, powders, granules, tablets, capsules, syrups, enteric coatings, inhalants, troches, ointments, suppositories and sublingual tablets. These formulations may be used alone or in combination thereof depending on the conditions of the subject. The preparation of the formulations can be performed by any of known methods using appropriate known additives which are conventionally used in medical formulation (e.g., excipients, binders, disintegrants, lubricants, flavorants), depending on the intended uses.

In administration of the peptide to a human as a medicine, the effective dose is not particularly limited and may vary depending on the degree of the effective activity of the peptide, the age, sex and body weight of a subject to be treated, and the conditions of the diseases of the subject. In the case of administration to an adult human, normally the dose may be appropriately selected within the range of 0.1 to 100 mg per day for oral administration or the range of 0.01 to 10 mg per day for parenteral administration.

EXAMPLES

The present invention will be further illustrated by the following examples. It is to be understood that the present invention is not limited to the examples.

Example 1

Purification of HsTX1 a. Crude Extraction 50 mg of lyophilized *Heterometrus spinnifer* venom gland (obtained from Latoxan, France) was homogenized with about 5 ml of a 0.5 M acetic acid solution and the homogenate was centrifuged at 3,000×g for 20 min. The precipitate was subjected to homogenization and centrifugation in the same manner three times. The resultant supernatant was passed through a 0.45 µm filter to obtain a crude extract.

b. Reversed-Phase Column Chromatography (1)

The crude extract obtained in step (a) above was subjected to C18-HPLC using Capcell pak C18 SG-120 (Shiseido Co., Ltd., φ10×250 mm) by batches of 12.5 mg, developed with a 0.1% aqueous TFA solution (pH 2.2) at a flow rate of 3 ml/min for 6 min, and then eluted with a linear gradient of acetonitrile in a 0.1% aqueous TFA solution from 0% to 50% in 100 min. While monitoring the UV absorbance at 230 nm, the fractions indicating the peak absorbance were pooled. These fractions were tested for the inhibitory activity on the rat brain Kv1.3 voltage-gated $K^+$ channels expressed in *Xenopus oocytes*, and the active fractions eluted at the retention times of 38–41 min were collected.

c. Cationic Ion Exchange Column Chromatography

The active fractions obtained in step (b) were dissolved in a 10 mM sodium phosphate buffer (pH 6.8). The resultant solution was subjected to cationic ion exchange column chromatography using TSK-gel SP-5PW (Tosoh Corporation, φ7.5×75 mm), developed in a 10 mM sodium phosphate buffer (pH 6.8) at a flow rate of 0.5 ml/min for 5 min, and then eluted with a linear gradient of NaCl from 0 M to 0.80 M in 80 min. While monitoring the UV absorbance at 230 nm, the fractions indicating the peak absorbance were pooled. These fractions were tested in the same manner as in step (b) and the active fractions eluted at the retention times of 64–69 min were collected.

d. Reversed-Phase Column Chromatography (2)

The active fraction obtained in step (C) was subjected to HPLC using C-18 column (Merck & Co., Inc., Lichrospher 100 angstroms, beads size: 5 µm, φ4×125 mm), developed with a 0.1% aqueous TFA solution (pH 2.2) at a flow rate of 1.0 ml/min for 3 min, and then eluted with a linear gradient of solvent B (a mix solution of 2-propanol:acetonitorile=2:1) in a 0.1% aqueous TFA solution from 5% to 18% in 35 min while monitoring the UV absorbance at 230 nm. HsTX1 was eluted as a single peak at a retention time of 27.5 min.

These fractions were pooled and then lyophilized to give HsTX1 in an overall yield of 130μg.

Example 2

Structure Determination of HsTX1 a. Determination of Amino Acid Composition

HsTX1 obtained in Example 1 was hydrolyzed with a constant boiling point 6N-HCl in a sealed tube at 110° C. for 20 hr and the resultant was subjected to determination of amino acid composition using an amino acid analyzer. The amino acid composition is shown in Table 1 below.

TABLE 1

Amino acid composition of HsTX1

| Amino acid | HsTX1 |
|---|---|
| Asx | 3.6(4) |
| Glx | 1.1(1) |
| Ser | 1.0(1) |
| Gly | 2.3(2) |
| His | 0 |
| Thr | 2.0(2) |
| Ala | 2.1(2) |
| Pro | 3.0(3) |
| Arg | 3.8(4) |
| Tyr | 0.8(1) |
| Val | 0 |
| Met | 0.9(1) |
| 1/2 cystine | 7.4(8) |
| Ile | 0 |
| Leu | 0 |
| Phe | 0 |
| Lys | 5.0(5) |

The numbers inside the parentheses indicate the number of residues determined by calculation.

b. Amino Acid Sequencing

Step 1: Reduction and Modification of Disulfide Bridges

HsTX1 was reacted with 5 equivalents of tributyl phosphine based on the number of the disulfide bridges and 2 equivalents of 4-vinylpyridine based on the amount of the tributyl phosphine in 20% n-propanol in a 0.5 M bicarbonate buffer at 37° C. for 2 hr in a nitrogen stream under the shaded condition, whereby Cys residues were S-pyridylethylated. The resultant S-pyridylethylated peptide (hereinafter, simply referred to as "PE-peptide") was purified by HPLC using C-18 column (Merck & Co., Inc., Lichrospher 100 angstroms, beads size: 5 μm, φ4×125 mm) with a linear gradient of acetonitrile in a 0.1% TFA/water mix solution from 5% to 60% in 55 min at a flow rate of 1.0 ml/min.

Step 2: Amino Acid Sequencing

The PE-peptide obtained in step 1 was subjected to determination of the amino acid sequence using Shimadzu PPSQ10 amino acid sequencer (Shimadzu Corp.). As a result, it was found that HsTX1 is a peptide represented by SEQ ID NO: 1 in which four disulfide bridges are present in the molecule.

Step 3: Determination of Molecular Weight

The molecular weight of HsTX1 determined by matrix assisted laser desorption-time of flight-mass spectrometry (MALDI-TOF-MS) was 3815.63. This result was in good agreement with the value determined by calculation for the formulation $C_{149}H_{246}N_{54}O_{46}S_9$ in which four disulfide bridges are present (3815.61).

Step 4: Determination of the Positions of Disulfide Bridges a) Partial reduction-alkylation and sequence determination Partial reduction-alkylation of HsTX1 was performed according to the method of Jones et al. (Jones et al., Rapid Commun. Mass Spectrum., vol. 10, pp. 138–143, 1996) with slight modification. Briefly, 2 to 3 nanomoles of HsTX1 obtained in Example 1 in 25 μl of a 0.1 M ammonium acetate/acetonitrile solution (90:10, pH 4) was incubated with 2 molar equivalents of tris-(2-carboxyethyl)-phosphine (TCEP) at 50° C. for 10 min. A 100 molar equivalents excess of N-phenyl-maleimide was then added to the mixture and reacted at 50° C. for 30 min. After adding 200 μl of a 0.1% aqueous TFA solution, the reaction mixture was applied to reversed-phase C-18 column (Merck & Co., Inc., Lichrospher, φ4×125 mm), and then eluted with a linear gradient of acetonitrile in a 0.1% aqueous TFA solution from 5% to 45% in 80 min at a flow rate of 1 ml/min. MALDI-TOF-MS analysis allowed to identify the partially reduced, alkylated peptide. This peptide was then sequenced without further reduction-alkylation procedures.

As a result of the MALDI-TOF-MS analysis of the partially reduced, alkylated peptide, it was confirmed that one of the disulfide bridges in the molecule was reduced and two alkylated cysteine residues were present. The 3-phenyl-2-thiohydantoin (PTH) derivative of alkylated cysteine residues were identified to be present at positions 19 and 34. These results revealed that one of the disulfide bridges present in HsTX1 is $Cys^{19}$-$Cys^{34}$.

b) Enzymatic cleavage

Tryptic cleavage of HsTX1 was performed using Poroszyme® immobilized trypsin cartridge (PerSeptive Biosystems, USA). Briefly, the cartridge was mounted onto an HPLC system in an oven set at 40° C., and then equilibrated in digestion buffer (10 mM $CaCl_2$, 50 mM Tris-HCl; pH 8):acetonitrile (95:5, v/v) at a flow rate of 1 ml/min. One nanomole of the synthetic HsTX1 synthesized in Example 3 below was dissolved in 50 μl of the digestion buffer and injected onto the column at a flow rate of 50 μl/min. A stop flow allowed a reaction time of 20 min. The reaction mixture was eluted with 3 column volumes (3×100 μl) of the digestion buffer:acetonitrile solution (95:5, v/v). The eluates were collected in a polyethylene tube containing 6 μl of 6N HCl (final pH: not more than 2) and then immediately stored at −80° C.

The resultant reaction mixture was applied to a reversed-phase C-18 column (Merck & Co., Inc., φ4×125 mm), eluted with a linear gradient of acetonitrile in a 0.1% aqueous TFA solution from 0% to 45% in 80 min at a flow rate of 1 ml/min. Three minutes after the elution was started, monitoring of the UV absorbance at 230 nm of each fraction was started and the fractions indicating peak values were collected. These fractions were lyophilized prior to physiochemical characterizations (i.e., mass spectrometry, sequencing). The tryptic fragment eluted at 24 min was further cleaved with AspN-endopeptidase (in 1 μl of 10 mM Tris-HCl, pH 8.1; the ratio of the peptidase to about 40 picomoles of peptide was about 4% w/w), and then subjected to the direct MALDI-TOF-MS determination on a microplate.

This enzymatic cleavage procedures gave four fragments. The yield of the reaction was quantitative and no random rearrangement of the intramolecular disulfide bridges was observed. The resultant fragments were subjected to mass spectrometry and sequencing to analyze the disulfide bridge pattern. As a result, it was revealed that the peptide which was obtained from the fractions digested with trypsin and eluted at 24 min contained two disulfide bridges including half cystine residues at positions 9, 13, 29 and 31. About 40 picomoles of the above fragments were further cleaved with AspN-endopeptidase and then subjected to the direct MALDI-TOF-MS determination on a microplate. The result showed that two of these fragments contained disulfide bridges corresponding to $Cys^{13}$-$Cys^{31}$ and $Cys^9$-$Cys^{29}$, respectively.

These results clearly show that HsTX1 of the present invention contains four disulfide bridges, $Cys^3$-$Cys^{24}$, $Cys^9$-$Cys^{29}$, $Cys^{13}$-$Cys^{31}$ and $Cys^{19}$-$Cys^{34}$.

Step 5: Conformational Analysis by Circular Dichroism

Circular dichroism (CD) spectra of the peptides of the present invention (i.e., natural HsTX1, synthetic HsTX1 obtained in Example 3 below and HsTX1-COOH which is a derivative of HsTX1 having the C-terminal of —COOH) and charybdotoxin (ChTX) (Peptide Institute, Inc., Japan) were determined using Jasco J-600 CD spectrometer (Jasco Corporation) with (+)-camphor 10-sulfonic acid as the standard.

In the determination, the spectra were measured in a 20 mM phosphate buffer (pH 7.1) at room temperature at 260–190 nm of wavelength using a 1 mm path length cell. Spectrum data were collected at 0.1 nm intervals with a scan rate of 100 nm/min for 500 min. The concentration of each peptide was made equal (80 μg/ml) by the aid of amino acid analysis. The data were expressed as molecular ellipticity per residue and analyzed by the method of Compton and Johnson (Anal Biochem., vol. 155, pp. 155–167, 1986).

The CD spectrum of each of the synthetic HsTX1 and HsTX1-COOH (peptides of the present invention) was almost the same as that of the natural HsTX1. When the CD spectrum of ChTX was compared with that of HsTX1 for comparison of the secondary structure therebetween, the minimum absorbance and the maximum absorbance of the ChTX CD spectrum were slightly shifted, with the minimum at 218 nm and the maximum at 195 nm (vs. 220 nm and 190 nm, respectively, for HsTX1).

These results revealed that ChTX and HsTX1-COOH, synthetic HsTX1 and natural HsTX1 of the present invention are all have α-helix (36, 29, 34 and 28%, respectively), β-sheet (18, 21, 20 and 20%, respectively) and β-turn (19, 14, 12 and 14%, respectively) therein. These structural analysis data show that the folded structure of HsTX1 is similar to that of ChTX.

It has been known that both Pi1 (supra.) and maurotoxin (Kharrat et al., Eur. J. Biochem., vol. 242, pp. 491–498, 1996) have the similar folded structure to that of ChTX, but maurotoxin has a specific disulfide bridge pattern. This fact illustrates the validity of the above-mentioned HsTX1 structure deduced by using the parameters of the ChTX.

Example 3

Synthesis of HsTX1 by Solid Phase Method

Synthesis of peptides was performed by FastMoc® solid phase method on an automatic 433A peptide synthesizer (Applied Biosystems) using Fmoc-aminoethyl-SAL resin (Watanabe Chemical Industries, Ltd.) as a support and Fmoc-Ala, Fmoc-Arg (Pmc), Fmoc-Asp (OtBu), Fmoc-Asn (Trt), Fmoc-Cys (Trt), Fmoc-Gly, Fmoc-Glu (OtBu), Fmoc-Lys (Boc), Fmoc-Met, Fmoc-Pro, Fmoc-Ser (tBu), Fmoc-Thr (tBu) and Fmoc-Tyr (tBu), wherein abbreviations used are as follows: Fmoc=9-fluorenylmethoxycarbonyl, SAL= super acid labile, Pmc=2,2,5,7,8-pentamethylchroman-6-sulfonyl, Trt=trityl, tBu=t-butyl, Boc=t-butyloxycarbonyl.

Procedures for cleavage of the peptide from the peptide-resin conjugate and deprotection of the crude peptide were performed by adding a TFA:thioanisole:ethandithiol (90:5:5, v/v) mix solution to the peptide-resin conjugate in an amount of about 10 ml per 1 g of the conjugate and then reacting the mixture at room temperature for 1.5 to 3 hr. To the resultant reaction solution was added diethyl ether to precipitate the peptide. The precipitate was washed with diethyl ether three times to give a crude peptide. The crude peptide was purified by reversed-phase C-18 HPLC.

The purified peptide was dissolved in a 0.5 mM Tris-HCl buffer (pH 8.2) supplemented with 1 mM oxidized glutathione and 1 mM reduced glutathione, and the solution was then exposed to air for 30 hr to oxidize the peptide, by which disulfide bridges were introduced into the peptide. After the oxidation reaction was completed, the reaction solution was subjected to HPLC using C-18 column (Merck & Co., Inc., Lichrospher 100 angstroms, beads size: 5 μm, φ4×125 mm), developed with 5% acetonitrile in a 0.1% aqueous TFA solution (pH 2.2) at a flow rate of 1.0 ml/min for 3 min, and then eluted with a linear gradient of acetonitrile in a 0.1% aqueous TFA solution from 5% to 20% in 30 min while monitoring the UV absorbance at 230 nm. Based on the fact that the natural HsTX1 is eluted with this HPLC system at the retention time of 26.6 min in a single peak, the peak fractions eluted at the same retention time (i.e., 26.6 min) were pooled to give synthetic HsTX1.

The obtained synthetic HsTX1 was mixed with the natural one, and the mixture was co-eluted in the same HPLC system as mentioned above. As a result, both natural and synthetic HsTX1s were detected at the retention time of 26.6 min in a single sharp peak. The molecular weight of the synthetic HsTX1 determined by MALDI-TOF-MS was 3815.67, which was in good agreement with that of the natural one (3815.63).

Example 4

Preparation for Injection Comprising HsTX1

One milligram of the synthetic HsTX1 obtained in Example 3 was dissolved in 20 ml of water for injection and the resultant solution was passed through a 0.22 μm filter for sterilization. Thereafter, the solution was packed into ampoules by 1 ml each under sterilized conditions, thus obtaining preparations for injection comprising HsTX1.

Evaluation Example 1

Assay of $K^+$ Channel Inhibition

Assay on inhibitory activity of the peptides on $K^+$ channels was performed in the following manner. The gene of the rat brain voltage-gated $K^+$ channel, Kv1.3 (Stuhmer et al., EMBO J., 8, vol. 11, pp. 3235–3244, 1988), which was graciously contributed by Prof. O. Pongs (Institute für Neurale Signalverarbeitung, Hamburg, Germany) was inserted into pAS18 vector according to a conventional technique. This vector was treated with EcoRI and then the resultant clone was transcribed in vitro with SP6 RNA polymerase using a transcription kit (Stratagene Inc., USA). The cRNA obtained was injected into *Xenopus oocytes* 16–72 hr prior to electrophysiological experiments.

The oocytes which had been expressed the Kv1.3 gene were added to a 100 μl-chamber filled with an ND96 solution (0.3 mM $CaCl_2$, 1 mM $MgCl_2$, 2 mM KCl and 96 mM NaCl in 5 mM Hepes buffer, pH 7.6) supplemented with 50 mg/ml of bovine serum albumin (BSA), and the ND96 solution was continuously perfused through reservoirs at a flow rate of 4 ml/min. The sample to be tested was separately dissolved to an ND96 solution and then added to the chamber by perfusion through a reservoir. The switching from one reservoir to another for each experiment was performed by means of Teflon valves. All measurements were made at room temperature (about 22° C.).

The oocytes were impaled by two microelectrodes filled with 3M KCl (internal resistance: 0.5–2 MΩ) and voltage-clamped using Axoclamp-2 two electrode voltage-clamp amplifier (Axon Instruments, Inc.) in a mode where the voltage of the chamber was clamped at 0V. Currents were low-pass filtered at 1 kHz using a 8 pole-Bessel filter (CyberAmp, Axon Instruments Inc.; –3dB), sampled and digitized at 10 kHz using Digidate 1200 Interface (Axon Instruments Inc.), and then saved the data to a photomagnetic disk for subsequent off-line analysis. Programming and recording of the potential and analysis of the saved data were performed by running Pclamp software (Axon Instruments Inc.) in a Compaq PC computer. The measurement was conducted with a holding potential of −80 mV and a holding current of not more than −40 nA.

As a result, it was found that HsTX1 of the present invention showed an extremely potent blocking action on the K$^+$ channels, i.e., the 50% blocking concentration (IC$_{50}$) of 12+1.6 pM, which is about 800 times stronger than Pi1 (supra.) which is another scorpion toxin exhibiting the same activity.

Evaluation Example 2

Activity of HsTX1 on Rat Kv1.3 Channels

Inhibitory activity of HsTX1 of the present invention on Kv1.3 channels was examined by measuring the concentration-dependent inhibition of the voltage-gated outward current on the voltage-gated K$^+$ channels expressed in *Xenopus oocyte* system. As a result, it was found that in the presence of 10 pM of HsTX1, the outward current was inhibited by nearly 50% at all voltages tested, compared with a control (without any peptide). Transient perfusion with 100 pM of HsTX1 followed by perfusion without any peptide like the control caused over 85% recovery of $K^+$ current over time. This result reveals that the inhibitory activity of HsTX1 on $K^+$ channel is almost reversible.

FIG. 1 shows the concentration-dependent inhibitory activity curve of the peptide of the present invention on the rat Kv1.3 channels.

As apparent from FIG. 1, it can be understood that the peptides of the present invention, i.e., natural HsTX1 and synthetic HsTX1 obtained in Example 3, show quite the same inhibition pattern, in which the 50% inhibition concentration ($IC_{50}$) was 12 pM for the natural HsTX1 and about 13 pM for the synthetic HsTX1 and both peptides exhibit an extremely potent inhibitory activity on the $K^+$ channels.

On the contrary, HsTX1-COOH, which is a derivative of HsTX1 with the C-terminal not amidated, showed $IC_{50}$ of 69 pM, which is about one-fifth of that for HsTX1 of the present invention. Accordingly, it can be understood that the peptides of the present invention can exhibit the inhibitory activity even when the C-terminal is —COOH, but amidation of the C-terminal enhances the specific inhibitory activity on $K^+$ channels.

Evaluation Example 3

Activity of HsTX1 on Other Voltage-gated $K^+$ Channels

Inhibitory activity of HsTX1 of the present invention on other voltage-gated $K^+$ channels was examined in the same manner. The channels tested were Kv1.1 and Kv1.6, both of which are subtypes of rat brain voltage-gated $K^+$ channel. The experiment in *Xenopus oocyte* system was performed in the same manner as mentioned above using the clones from the Kv1.1 and Kv1.6 genes. Although both Kv1.1 and Kv1.6 channels were blocked by the synthetic HsTX1, $IC_{50}$ for both channels was about 300 pM, which is about one-thirty smaller than that for Kv1.3 channel.

As a result, it was revealed that HsTX1 of the present invention exhibits a specific blocking activity on Kv1.3 channels.

Evaluation Example 4

Activity of HsTX1 on IL-2 Production by Human Peripheral Blood T Cells

Inhibitory activity of HsTX1 on IL-2 production by activated T cells was examined in the following manner. Mononuclear leukocytes were isolated from heparinized peripheral blood from a normal donor by a centrifugation technique with a mono-poly resolving medium (Dainippon Pharmaceuticals Co., Ltd.), and then applied to a nylon wool column. The column was incubated at 37° C. for 30 min and then non-adherent cells were isolated therefrom. The purified T-cells obtained were suspended in RPMI 1640 medium supplemented with 10% inactivated fetal calf serum, 100 U/ml of penicillin and 100 μg/ml of streptomycin. This suspension was plated onto a 96-well flat-bottom plate in a final concentration of 1×1 $^6$ cells/ml, 1 ng/ml of phorbol myristate acetate (PMA) and 250 ng/ml of ionomycin were further added thereto as stimulators, and the plate was cultivated in a 5% $CO_2$ gas incubator at 37° C.

At the time of starting of cultivation, HsTX1 was added to each well in concentrations of 0.1, 1, 10 and 100 nM, respectively, to the final volume for each well of 200 μl. After 20 hr, the culture supernatant was collected and then determined for IL-2 concentration therein using a human IL-2 ELISA kit (Endogen).

The results are shown in FIG. 2.

As apparent from FIG. 2, HsTX1 of the present invention significantly inhibited the IL-2 production by human peripheral T cells at all of the above concentrations (Dunnett's test).

The inhibition rate of HsTX1 of the present invention against IL-2 production at concentrations of 0.1, 1, 10 and 100 nM were 28.6, 45.7, 46.0 and 46.7%, respectively.

In the examples and evaluation examples mentioned above, the present inventors succeeded in isolation and synthesis of a new class of scorpion toxin-related peptide, named HsTX1, and also succeeded in making clear the primary and higher-order structures of the peptides and the physiological activities on voltage-gated $K^+$ channels and IL-2 production inhibition thereof. Accordingly, peptides having similar primary and/or higher-order structures to those of HsTX1, even if they include deletions, additions or substitutions of a portion of the amino acid, are also covered within the technical scope of the present invention as peptides having blocking activity on voltage-gated $K^+$ channels and inhibitory activity on IL-2 production.

Industrial Applicability

According to the present invention, there can be provided, as scorpion toxin-related peptides, peptides represented by SEQ ID NO: 1 in which 0–4 disulfide bridges are present and their related peptides. Among them, HsTX1 is the first discovered one of neuropeptides having four disulfide bridges in the molecule and composed of 34 amino acid residues. Based on the fact that the inhibitory activity of HsTX1 on Kv1.3 channels is almost reversible, it is expected that HsTX1 has a satisfactorily low toxicity.

Among the peptides according to the present invention, HsTX1 significantly inhibited the IL-2 production by human peripheral blood T cells at a concentration of at least 0.1 nM. Since IL-2 is a cytokine which promoted the differentiation and proliferation of T cells, such inhibition of IL-2 production would lead to the inhibition of T cell activation.

According, the peptides of the present invention and their analogues are expected to contribute to application of scorpion toxin-related peptides to biochemical reagents in neurophysiology as well as application to human and veterinary medicines including those for graft-versus-host diseases (GVHD), autoimmune diseases and organ transplantation.

What is claimed is:

1. An isolated polypeptide comprising the amino acid sequence of SEQ ID NO:1.

2. The polypeptide of claim 1, wherein the polypeptide has up to four disulfide bonds.

3. The polypeptide of claim 2, wherein the disulfide bonds are $Cys^3$-$Cys^{24}$, $Cys^9$-$Cys^{29}$, $Cys^{13}$-$Cys^{31}$ or $Cys^9$-$Cys^{34}$.

4. The polypeptide of claim 1, 2, or 3, wherein the C-terminus of the polypeptide is amidated.

5. A voltage-gated $K^+$ channel blocking agent comprising a polypeptide of claim 1, 2, or 3.

6. An interleukin-2 production inhibitor comprising a polypeptide of claim 1, 2, or 3.

7. A pharmaceutical composition comprising a polypeptide of claim 1, 2, or 3.

* * * * *